(12) United States Patent
Tankhilevich et al.

(10) Patent No.: US 8,891,335 B2
(45) Date of Patent: Nov. 18, 2014

(54) GENERATION OF ULTRA-HIGH FREQUENCY SOUND

(71) Applicant: Laserphon, Inc., Walnut Creek, CA (US)

(72) Inventors: Boris G. Tankhilevich, Walnut Creek, CA (US); Yehiel Korenblit, Netanya (IL)

(*) Notice: Subject to any disclaimer, the term of this patent is extended or adjusted under 35 U.S.C. 154(b) by 134 days.

(21) Appl. No.: 13/661,053

(22) Filed: Oct. 26, 2012

(65) Prior Publication Data

US 2014/0119161 A1 May 1, 2014

(51) Int. Cl.
*G01K 11/00* (2006.01)
*B06B 1/00* (2006.01)
*H04B 11/00* (2006.01)

(52) U.S. Cl.
CPC . *H04B 11/00* (2013.01); *B06B 1/00* (2013.01)
USPC .......................................... 367/140; 381/150

(58) Field of Classification Search
None
See application file for complete search history.

(56) References Cited

U.S. PATENT DOCUMENTS

| | | | |
|---|---|---|---|
| 3,405,374 A * | 10/1968 | Dayem et al. | 333/147 |
| 7,411,445 B2 | 8/2008 | Kucherov et al. | |
| 7,430,074 B2 | 9/2008 | Korenblit et al. | |
| 7,507,302 B2 | 3/2009 | Miyoshi et al. | |
| 7,508,578 B2 | 3/2009 | Korenblit et al. | |
| 7,649,679 B2 | 1/2010 | Ajiki et al. | |
| 7,986,454 B1 | 7/2011 | Korenblit et al. | |
| 2010/0019798 A1 | 1/2010 | Saito et al. | |
| 2011/0101250 A1 | 5/2011 | Hu | |

OTHER PUBLICATIONS

Coey et al. "Half-metallic ferromagnetism: Example of $CrO_2$", Journal of Applied Physics, vol. 91, No. 10, pp. 8345-8350, May 2002.
Shan et al. "Demonstration of Half-Metallicity in Fermi-Level-Tuned Heusler Alloy CO2FeAl0.5Si0.5 at Room Temperature", Physical Review Letters 102, 246601, Jun. 19, 2009.
Korenblit et al. "Generation of High-Frequency Magnons by NonEquilibrium Electrons Polarized Opposite to the Direction of Magnetization", Soviet Physics, JETP, vol. 46(6), pp. 1167-1175, Dec. 1977.
Korenblit et al. "Generation of High-Frequency Magnons in a Ferromagnetic Semiconductor", Pis'ma Zh. Eksp. Teor. Fiz. 24, No. 11, pp. 598-601, Dec. 1976.
Korenblit et al. "High Frequency Magnon Generation by NonEquilibrium Electrons and the Instability of the Magnon System", Physics Letters, vol. 64A, No. 3, pp. 307-308, Dec. 1977.
Akhiezer et al. "Spin Waves", North-Holland Series in Low Temperature Physics, vol. 1, pp. 268-275, 1968.

(Continued)

*Primary Examiner* — Isam Alsomiri
*Assistant Examiner* — Hovhannes Baghdasaryan
(74) *Attorney, Agent, or Firm* — Boris G. Tankhilevich

(57) ABSTRACT

An apparatus for generating ultra-high frequency sound waves with frequencies between (1 GHz-10 GHz) is proposed. The apparatus comprises a magnetic phonon-gain medium configured to generate high frequency non-equilibrium phonons by non-equilibrium magnons having the magnon velocity exceeding the sound velocity in the magnetic phonon-gain medium. The non-equilibrium magnons having the magnon velocity exceeding the sound velocity in the magnetic phonon-gain medium are generated by injected non-equilibrium electrons having spin opposite to the direction of magnetization of the magnetic phonon-gain medium. The apparatus further comprises a means for outputting the ultra-high frequency non-equilibrium phonons.

36 Claims, 6 Drawing Sheets

(56) References Cited

OTHER PUBLICATIONS

Wurmehl et al. "Geometric, electric, and magnetic structure of Co2FeSi: Curie temperature and magnetic moment measurements and calculations", Physical Review B 72, 184434, 2005.

Kittel "Quantum Theory of Solids", John Wiley & Sons, Inc., 1963.

Swartz "Thermal boundary resistance", Reviews of Modern Physics, vol. 61, No. 3, pp. 605-668, Jul. 1989.

* cited by examiner

FIG. 1 Schematic density of states for a half metal, Type IA with only electrons with spin up at $E_f$ (Coey and Venkatesn, J. Appl. Phys. 91, 8345 (2002)).

GENERATION OF ULTRA-HIGH FREQUENCY SOUND

TECHNICAL FIELD

The technology relates to the generation of ultra-high frequency sound in the GHz region.

BACKGROUND

The conventional ultrasound imaging (sonography) uses high-frequency sound waves to view soft tissues such as muscles and internal organs. Because ultrasound images are captured in real-time, they can show movement of the body's internal organs as well as blood flowing through blood vessels.

In an ultrasound exam, a hand-held transducer is placed against the skin. The transducer sends out high frequency sound waves that reflect off of body structures. The returning sound waves, or echoes, are displayed as an image on a monitor. The image is based on the frequency and strength (amplitude) of the sound signal and the time it takes to return from the patient to the transducer. Unlike with an x-ray, there is no ionizing radiation exposure with this test The conventional ultrasound imaging is used in many types of examinations and procedures. Some examples include: (a) Doppler ultrasound (to visualize blood flow through a blood vessel); (b) Bone sonography (to diagnose osteoporosis); (c) Echocardiogram (to view the heart); (d) Fetal ultrasound (to view the fetus in pregnancy); (e) Ultrasound-guided biopsies; (g) Doppler fetal heart rate monitors (to listen to the fetal heart beat).

The conventional ultrasound imaging has been used for over 20 years and has an excellent safety record. It is non-ionizing radiation, so it does not have the same risks as x-rays or other types of ionizing radiation.

The conventional ultrasound imaging is based on piezoelectric effect. A transducer is a very important part of the ultrasonic instrumentation system. The transducer incorporates a piezoelectric element, which converts electrical signals into mechanical vibrations (transmit mode) and mechanical vibrations into electrical signals (receive mode).

The conventional ultrasound imaging employs different frequencies. Lower frequencies between (0.5 MHz-2.25 MHz) provide greater energy and penetration in a material, while high frequency crystals that generate ultrasound in the range of (15.0 MHz-25.0 MHz) provide reduced penetration but greater sensitivity to small discontinuities.

High frequency transducers, when used with the proper instrumentation, can improve flaw resolution and thickness measurement capabilities dramatically. Broadband transducers with frequencies up to 150 MHz are commercially available.

There are also new medical procedures using High-Intensity Focused Ultrasound. High-Intensity Focused Ultrasound (HIFU, or sometimes FUS) is a highly precise medical procedure that applies high-intensity focused sonic energy to locally heat and destroy diseased or damaged tissue through ablation.

HIFU is also one modality of therapeutic ultrasound, involving minimally invasive or non-invasive methods to direct acoustic energy into the body. In addition to HIFU, other modalities include ultrasound-assisted drug delivery, ultrasound hemostasis, ultrasound lithotripsy, and ultrasound-assisted thrombolysis.

Clinical HIFU procedures are typically performed in conjunction with an imaging procedure to enable treatment planning and targeting before applying a therapeutic or ablative levels of ultrasound energy. When Magnetic resonance imaging (MRI) is used for guidance, the technique is sometimes called Magnetic Resonance-guided Focused Ultrasound, often shortened to MRgHIFU or MRgFUS. When diagnostic sonography is used, the technique is sometimes called Ultrasound-guided Focused Ultrasound (USgHIFU or USgFUS).

Currently, MRgHIFU is an approved therapeutic procedure to treat uterine fibroids in Asia, Australia, Canada, Europe, Israel and the United States. USgHIFU is approved for use in Bulgaria, China, Hong Kong, Italy, Japan, Korea, Malaysia, Mexico, Russia, Romania, Spain and the United Kingdom. Research for other indications is actively underway, including clinical trials evaluating the effectiveness of HIFU for the treatment of cancers of the brain, breast, liver, bone, and prostate.

In the present patent application, we propose a new technique to generate ultra-sound having ultra-high frequency up to GHz. This ultra-sound frequency is at least an order of magnitude higher that the max sound frequency achieved so far.

The proposed technique has the potential to create a new field of ultra-high frequency ultra sound imaging and treatment.

SUMMARY

This Summary is provided to introduce a selection of concepts that are further described below in the Detailed Description. This Summary is not intended to identify key or essential features of the claimed subject matter, nor is it intended to be used as an aid in determining the scope of the claimed subject matter.

An apparatus for generating ultra-high frequency sound waves frequencies up to GHz is proposed.

The apparatus of the present technology comprises: (A) a magnetic phonon-gain medium configured to generate high frequency non-equilibrium phonons by non-equilibrium magnons having the magnon velocity exceeding the sound velocity in the magnetic phonon-gain medium. The non-equilibrium magnons having the magnon velocity exceeding the sound velocity in the magnetic phonon-gain medium are generated by injected non-equilibrium electrons having spin opposite to the direction of magnetization of the magnetic phonon-gain medium.

The apparatus of the present technology further comprises: (B) means for outputting the ultra-high frequency non-equilibrium phonons.

DESCRIPTION OF THE DRAWINGS

The accompanying drawings, which are incorporated in and form a part of this specification, illustrate embodiments of the technology and, together with the description, serve to explain the principles below.

DETAILED DESCRIPTION

Reference now is made in detail to the embodiments of the technology, examples of which are illustrated in the accompanying drawings. While the present technology will be described in conjunction with the various embodiments, it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following detailed description, numerous specific-details are set forth in order to provide a thorough understanding of the presented embodiments. However, it will be obvious to one of ordinary skill in the art that the presented embodiments may be practiced without these specific details. In other instances, well known methods, procedures, components, and circuits have not been described in detail as not to unnecessarily obscure aspects of the presented embodiments.

I. Cherenkov Type Phonon Excitation by Magnons

We propose a method for generating ultra-high-frequency sound, with frequency of GHz and higher, in spin-polarized ferromagnetic materials like half-metals. In these materials the conduction bands are split by the exchange interaction into two sub bands with opposite spin orientation, and only electron states in the lower sub band ("spin up" majority electron states) are occupied at zero temperature.

Figure 1:
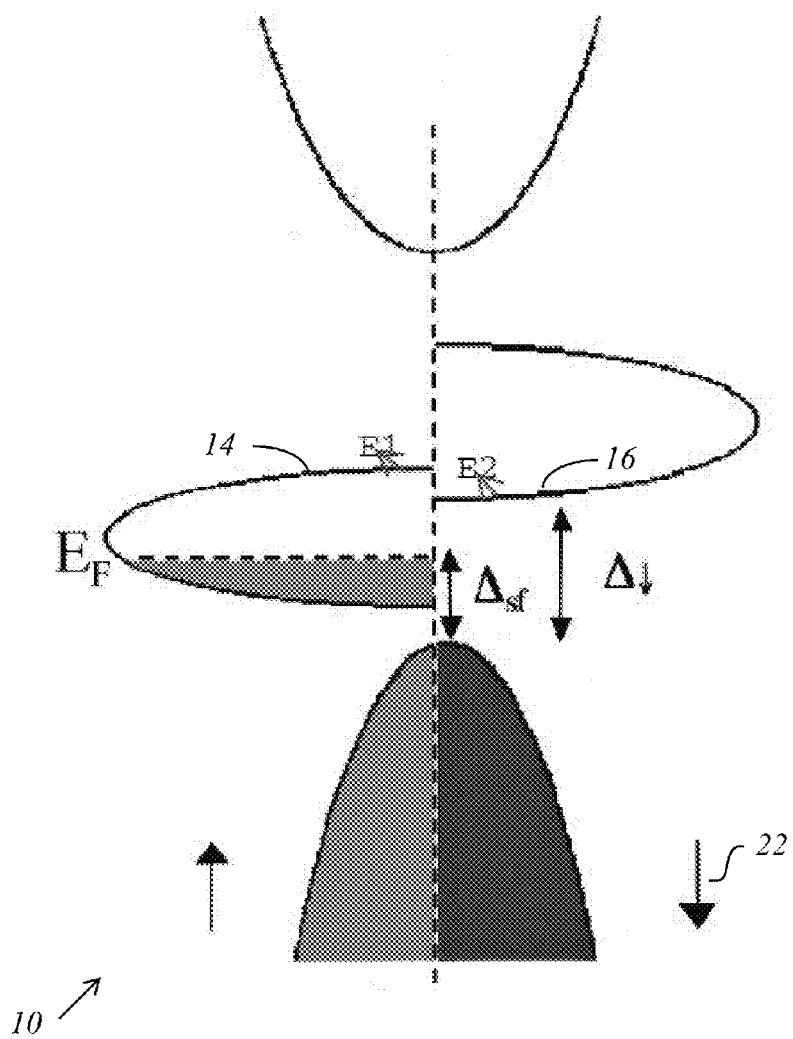
FIG. 1 depicts the schematic density of states for a half metal, Type IA with only electrons with spin up at Fermi energy level $E_f$ (Coey and Venkatesn, *J. Appl Phys.* 91, 8345 (2002).

In an embodiment of the present technology, FIG. 1 depicts the schematic density of states 10 for a half metal, Type IA with only electrons with spin up at Fermi energy level $E_f$ 12 (Coey and Venkatesn, *J. Appl Phys.* 91, 8345 (2002).

In some half-metals the electrons are almost fully polarized even at room temperature, e.g., in the Heusler alloy Co2FeAl0.5Si0.5 the spin polarization is as high as 0.91 at 300 K. Please, see R. Shan et al, *Phys. Rev. Lett.* 102, 246601 (2009).

Non-equilibrium electrons pumped into the upper sub band ("spin-down" minority electron states) rapidly emit magnons, with frequencies in the THz region. For example, as shown in FIG. 1, electrons from states 14 and having energy E1 and spin up by transitioning into states with energy 16 and spin down 22 emit magnons.

In an embodiment of the present technology, at critical pumping currents of order of $(10^5\text{-}10^6)$ A/cm$^2$ the number of magnons in a smooth frequency interval increases exponentially with pumping. For more details, please see I. Ya. Korenblit and B. G. Tankhilevich, *Sov. Phys.—JETP,* 46, 1167 (1977); I. Ya. Korenblit and B. G. Tankhilevich, *Sov. Phys.—JETP Lett.* 24, 555 (1976); I. Ya. Korenblit and B. G. Tankhilevich, *Phys. Lett. A* 64, 307 (1977).

Figure 2:
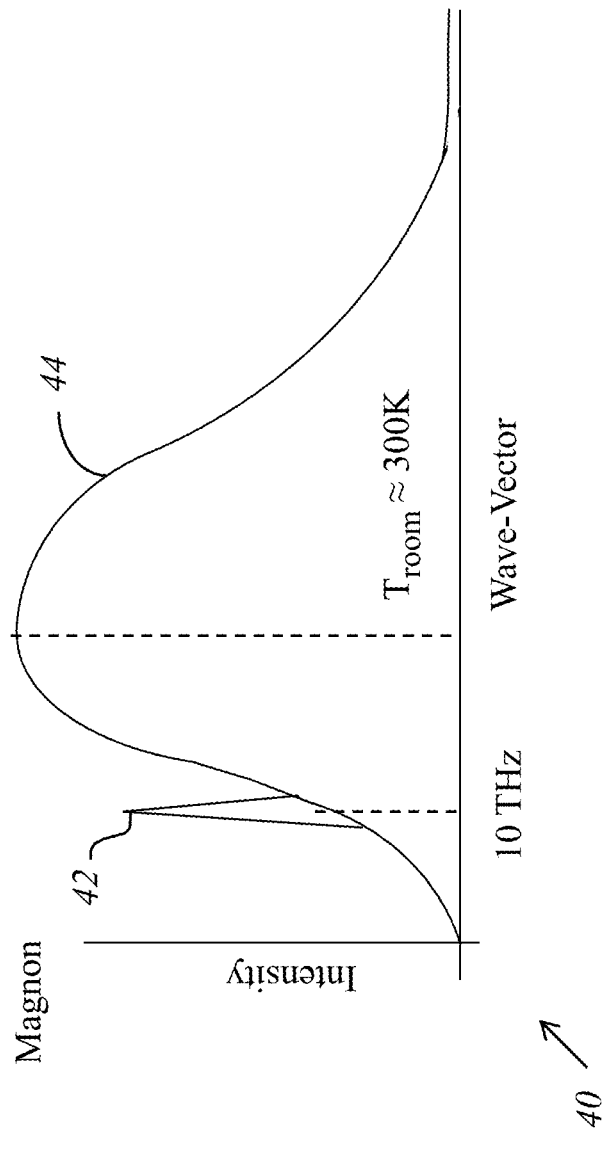
FIG. 2 shows a peak of non-equilibrium magnons superimposed on Bose-Einstein Spectrum of Equilibrium Magnons for the purposes of the present technology.

FIG. 2 40 shows a peak 42 of non-equilibrium magnons superimposed on Bose-Einstein Spectrum of Equilibrium Magnons 44 for the purposes of the present technology.

In an embodiment of the present technology, magnons with sufficiently high frequency and, hence, large velocity can emit sound waves (phonons) in a process akin to Cherenkov radiation of electromagnetic waves by fast electrons.

Figure 3:
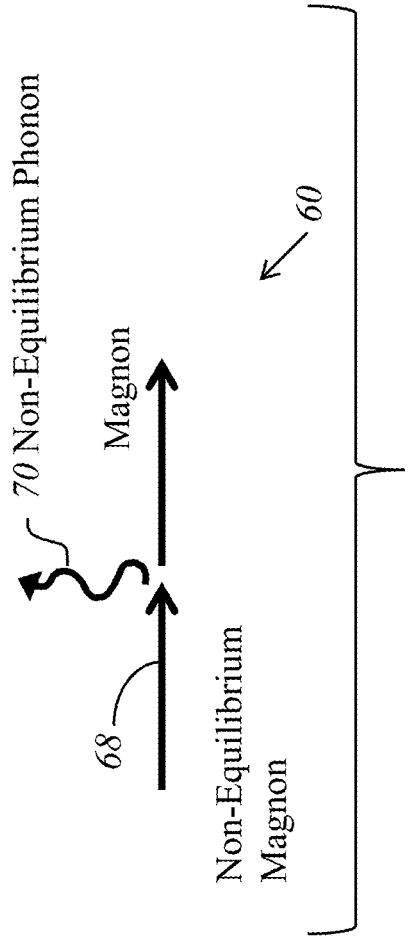
FIG. 3 illustrates generation of a non-equilibrium phonon by a non-equilibrium magnon having velocity that exceeds the sound velocity in the magnetic phonon-gain medium for the purposes of the present technology.

In an embodiment of the present technology, FIG. 3 illustrates a Feynman diagram 60 of generation of a non-equilibrium phonon 70 by a non-equilibrium magnon 68 having velocity $v_m$ that exceeds the sound velocity u in the magnetic phonon-gain medium.

The spectrum of the magnons is $$\epsilon(q) = \hbar\,\Omega(q) = Dq^2, \qquad (1)$$

where $\epsilon(q)$ and $\Omega(q)$ are respectively the energy and the frequency of the magnon, q is the magnon wave vector, D is the magnon stiffness, and $\hbar$ is the Plank constant.

Hence, the magnon velocity is $v_m = 2Dq/\hbar$. and the sound wave excitation takes place if the magnon frequency $\Omega_q = 2\pi f_q$ satisfies the following inequality $$\Omega_q \geq \hbar\, u^2/4D. \qquad (2)$$

For the reference, please, see A. I. Alchiezer, V. G. Baryalchtar, and S. V. Peletminskii, *Spin Waves,* Amsterdam: North-Holland, (1968), pages (268-275).

In an embodiment of the present technology, in half-metals, with Curie temperatures, Tc, higher than the room temperature, the stiffness varies from D≈100 meV·Å$^2$ in chromium dioxide (Tc=390 K) (please, see the reference J. M. D. Coey and M Venkatesan, *J. Appl. Phys.* 91, 8345 (2002)) to D≈370 meV·Å$^2$ in Heusler alloy Co2FeAl ($T_c$≈1000 K) (please, see the reference S. Wurmel et al., *Phys. Rev.* 72, 184434 (2005)).

In an embodiment of the present technology, assuming for the sound velocity a typical value u=5·10$^5$ cm/s, one can deduct, that magnons, with frequencies larger than several THz, emit phonons in the Cherenkov process.

In an embodiment of the present technology, in a conductor with a simple parabolic electron band the non-equilibrium electrons emit magnons in a smooth wave vector interval $q_0 - \kappa \leq q_0 + \kappa$, where $\hbar\, q_0 = \sqrt{(2m\Delta)}$, m is the electron mass, $\Delta$ is the electron exchange gap, and p=$\hbar$ κ is the momentum of the electrons in the upper (spin-down) sub band, while it is supposed that κ/qo is small. Thus, the frequency of the excited magnons is close to the value $\Omega(q_0) = 2m D\Delta/\hbar^3$. With the above values of D and with Δ≈0.5 eV and m equal the free electron mass, one gets $\Omega(q_0)$=50-150 THz. In what follows we shall use for numerical estimates the value $\Omega(q_0)$=5×10$^{13}$ sec$^{-1}$.

II. Magnon-Phonon Interaction

The probability, $W(q, q_1, k)$ that a magnon with wave-vector q excites a phonon with wave-vector k and frequency $\omega_k = uk$, and transforms into a magnon with wave-vector $q_1$ reads. Please, see A. I. Akhiezer, V. G. Baryakhtar, and S. V. Peletminskii, *Spin Waves*, Amsterdam: North-Holland, (1968), pages (268-275).

$$W(q,q_1,k) = 2\pi\hbar^{-1}|\Psi(q,q_1,k)|^2 N_q(N_{q_1}+1)(n_k+1)$$
$$\delta(\epsilon_q - \epsilon_{q_1} - \hbar\omega_k)\delta(q - q_1 - k) \quad (3)$$

Here $N_q$ and $n_k$ are respectively the distribution function of the magnons and phonons, and the amplitude $\Psi$ is given by:

$$\Psi = bDa^{-3/2}\hbar^{1/2}(\rho\omega_k)^{-1/2}qq_1k, \quad (4)$$

where a is the lattice constant, $\rho$ is the material density, and b is a constant of order unity.

Thus, the change of the number of phonons with time due to the phonon-magnon interaction can be written as $$(\partial n_k/\partial t)_{mf} = 2\pi\hbar^{-1}(a/2\pi\hbar)^3\int d^3q |\Psi|^2 [(N(\epsilon_q)(N(\epsilon_q - \hbar\omega_k) + 1)(n(\omega_k) + 1)(-)n(\omega_k)N(\epsilon_q - \hbar\omega_k)(N(\epsilon_q) + 1)]\delta(\epsilon_q - \epsilon_{q-k} - \hbar\omega_k)$$

$$= 2\pi\hbar^{-1}(a/2\pi\hbar)^3\int d^3q |\Psi|^2 [(N(\epsilon_q)(N(\epsilon_q - \hbar\omega_k) + n(\omega_k) + 1)(-)N(\epsilon_q - \hbar\omega_k)n(\omega_k)]\delta(\epsilon_q - \epsilon_{q-k} - \hbar\omega_k), \quad (5)$$

with $|\Psi|^2$ given by $$|\Psi|^2 = \hbar k^2 b^2 a^{-3}(\rho\omega_k)^{-1}(\epsilon_q - \hbar\omega_k) \quad (6)$$

It follows from the energy conservation law that the angle, $\theta$, between the direction of the magnon wave vector, q, and the phonon wave vector, k, is:

$$\cos\theta = (k/2q) + (u/v_m) \quad (7)$$

This equation shows that, as noticed before, the phonon emission takes place only if u is less than $v_m$, while the phonon wave vector k varies from $k=0$ till $k=2q(1-u/v_m)$.

In an embodiment of the present technology, we are looking for an instability in the phonon system, when n increases exponentially with time. Therefore only terms proportional to n are important in the left side of the equation (6), and we get $$(\partial n_k/\partial t)_{mf} = (n_k/\tau_{mf}), \quad (8)$$

where the magnon-phonon relaxation time $\tau_{mf}$ is given by $$1/\tau_{mf} = 2\pi\hbar^{-1}(a/2\pi\hbar)^3\int d^3q |\Psi|^2 [(N(\epsilon_q - (N(\epsilon_q - \hbar\omega_k)]\delta(\epsilon_q - \epsilon_{q-k} - \hbar\omega_k). \quad (9)$$

In an embodiment of the present technology, we consider in what follows only isotropic systems. Then, as shown in I Ya. Korenblit and B. G. Tankhilevich, *Sov. Phys.—JETP*, 46, 1167 (1977); I. Ya. Korenblit and B. G. Tankhilevich, *Sov. Phys.—JETP Lett.* 24, 555 (1976); I. Ya. Korenblit and B. G. Tankhilevich, *Phys. Lett. A* 64, 307(1977), the non-equilibrium distribution function of magnons is:

$$N_q = [N^{(0)}_q + 1][(q/(q - \kappa^{s+1} - 1) + (\kappa/q_0)\exp(-g/g_c)]^{-1} \gg N^{(0)}_q, \quad (10)$$

if q belongs to the interval $q_0 - \kappa \leq q_0 + \kappa$, and $Nq = N^{(0)}_q$ for other wave-vectors.

Here g is the intensity of electron pumping, and is the critical pumping, s is the exponent in the q-dependence of the magnon-magnon relaxation time: $s=3$ for magnons with energy $\epsilon_q$ larger than $k_BT$, and $s=4$ for magnons with energy $\epsilon_q$ smaller than $k_BT$, wherein kg is Boltzmann constant. The relation (10) holds at sufficiently high pumping intensity $g \gg g_c$.

In an embodiment of the present technology, the typical energy of excited magnons exceeds $k_BT$. Therefore in what follows we put $s=3$ and we neglect $N^{(0)}_{q0}$ in comparison with unity. If the energy of excited magnons less than $k_BT$ the same approximation can be used.

In an embodiment of the present technology, if the inequality $$\omega_k > \Omega(q_0 + k) - \Omega(q_0 - k) \approx (4k/q_0)\Omega(q_0) \ll \Omega(q_0) \quad (11)$$

holds, the magnons with energy $(\epsilon_q - \hbar\omega_k)$ are outside the non-equilibrium region, and therefore $N(\epsilon_q - \hbar\omega_k)$ in Eq (9) may be neglected. As shown FIG. 3, this implies that only direct processes 60 of phonon 70 excitation by non-equilibrium magnons 68 take place, while the opposite processes of phonon absorption (not shown) do not matter.

Substituting Nq from Eq (10) into Eq (9), one gets in this case:

$$1/\tau_{mf} = (16\pi)^{-1}\hbar^3(\rho u)^{-1}D^{-2}\Omega(q_0)^3(g/g_c), \omega_k > (4k/q_0)\Omega(q_0). \quad (12)$$

Here and in what follows we ignore the constant $b \approx 1$. Note that $\tau_{mf}$ does not depend on the phonon frequency.

In an embodiment of the present technology, $\omega_k$ is smaller than $(4k/q_0)\Omega(q_0)$, the absorption processes reduces the overall generation rate of phonons, and the phonon generation frequency $(1/\tau_{mf})$ decreases with the decrease of wk:

$$1/\tau_{mf} = (64\pi)^{-1}\hbar^3(\rho uk)^{-1}D^{-2}\Omega(q_0)^2 q_0\omega_k, \omega_k \ll (4k/q_0)\Omega(q_0). \quad (13)$$

III. Phonon Instability

The change of $n_k$ with time is governed by the equation:

$$(\partial n_k/\partial t) = (n_k/\tau_{mf}) - ((n_k - n^0_k)/\tau) = 0. \quad (14)$$

The second term in the r.h.s. of the equation (14) describes the relaxation of $n_k$ to its equilibrium value $n^0k$, and $\tau$ can be written as:

$$\tau^{-1} = (\tau_{fe})^{-1} + (\tau_{ff})^{-1} + (\tau_{fi})^{-1} + (\tau_{fb})^{-1}, \quad (15)$$

where the relaxation times $\tau_{fe}$, $\tau_{ff}$, $\tau_{fi}$, and $\tau_{fb}$ are due to electron-phonon, phonon-phonon, mass-difference impurity scattering, and boundary scattering, respectively.

It follows from Eq (14) that $n_k$ increases exponentially with time $$N = C\exp[(\tau^{-1}_{mf} - \tau^{-1})t] \quad (16)$$

if $\tau^{-1}_{mf}$ is larger than $\tau^{-1}$, i.e. if the phonon generation by magnons exceeds their absorption.

In an embodiment of the present technology, the phonon relaxation in metals is mainly due to phonon-electron and boundary scattering. The relaxation time $\tau_{fe}$ is (please, see C. Kittel, *Quantum Theory of Solids*, J. Willey and Sons, N.Y.-London (1963)) pages (326-329)):

$$1/\tau_{fe} = 2(9\pi)^{-1}\hbar^{-3}(\pi u)^{-1}E^2_f(m)^2\omega_k, (k1 \gg 1) \quad (17)$$

and $$1/\tau_{fe} = 8(15)^{-1}(\rho v u^2)^{-1}nE_f l\omega^2_k, (k1 \ll 1) \quad (18)$$

where $E_f$ is the electron Fermi energy, I is the electron mean-free path, and n is the electron concentration.

In an embodiment of the present technology, at very high phonon frequencies, when the inequality (11) is fulfilled, the phonon-electron relaxation is given by the first of the above equations, and the ratio $\tau_{fe}/\tau_{mf}$ is given by:

$$\tau_{fe}/\tau_{mf} = \Delta^2(g/4g_c)E^{-2}_f q_0\kappa^{-1}. \quad (19)$$

This ratio is larger than unity only for very large $(q_0/K)$ and very high levels of pumping. Thus, it would be difficult to achieve the instability of the phonon system at such frequencies.

In an embodiment of the present technology, for lower phonon frequencies the phonon-electron relaxation decreases with frequency as ($\omega^2_k$, see Eq. (18)), while the phonon generation decreases as $\omega_k$. Therefore, at sufficiently low frequencies, the phonon generation by magnons exceeds their absorption by electrons. This happens at frequencies less than $\omega_k$=(1-10)×10$^{10}$ sec$^{-1}$.

But at these frequencies the boundary scattering which does not depend on frequency may compete with the phonon-electron scattering. It is usually assumed that the boundary scattering takes place without change of energy and without change in the number of phonons. Only transmission of phonons into the environment decreases $n_k$. The transmission coefficient depends on the mismatch in sound velocities and densities of the ferromagnet and of the environment, and it is small, when the mismatch is large (please, see E. T. Swartz and R. O. Pohl, *Rev. Mod. Phys.* 61, 605 (1983)). Therefore, the boundary relaxation time can be written as $$\tau_{fb}^{-1} = L\mu/u, \quad (20)$$

where L is the dimension of the system and $\mu \ll 1$ is the transition coefficient. We suppose that $\mu$ does not depend on the phonon frequency.

It follows than from Eqs. (13), (18) and (20) that the instability relation $$\tau_{mf}^{-1} \geq \tau_{fe}^{-1} + \tau_{fb}^{-1}, \quad (21)$$

is satisfied if the sample dimension L is larger than the following value $$L \geq (8\pi\kappa \hbar^3 \Delta^{-2} q_0^{-1})^2 n \rho v u m^{-5/2} \mu \approx 10^7 \mu l. \quad (22)$$

With $l \approx (10^{-5}-10^{-4})$ cm, and $\mu=10^{-3}$, one gets $L \geq L_c \approx (10^{-1}-10^{-2})$ cm.

Figure 5:
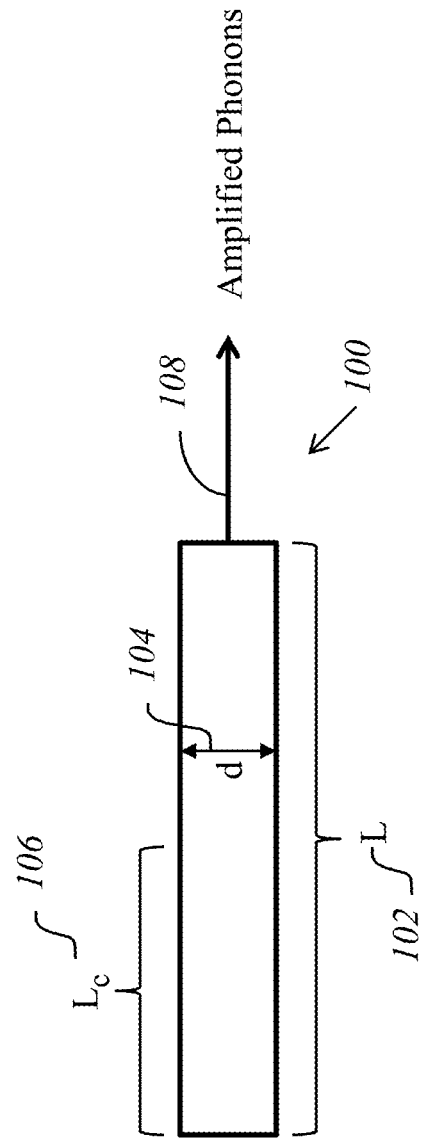
FIG. 5 shows optimal geometrical dimensions of the magnetic phonon-gain medium whereas the amplified ultra-high frequency phonons are generated in the longitudinal direction for the purposes of the present technology.

In an embodiment of the present technology, as shown in FIG. 5, one can prepare samples 100 in form of stripes, with the longitudinal dimension L 102 larger than $L_c$ 106, while the transverse dimensions d 104 smaller than $L_c$. Then, only phonons 108 moving in the longitudinal direction will be amplified, and one gets a strong stream of high-frequency sound.

In an embodiment of the present technology, when the parameters are such that Eq (21) the equality takes place, only one frequency, $\omega^*$, given by the relation $$\omega^* = (m\Delta^2 q_0 \mu)/(2\pi\kappa \hbar^3 nvl) \approx (1-10)10^9 \text{ sec}^{-1}, \quad (23)$$

is unstable, At parameters, satisfying the inequality (21), there exists a frequency interval $\omega_1 < \omega^* < \omega_2$ which becomes unstable under pumping.

Figure 4:
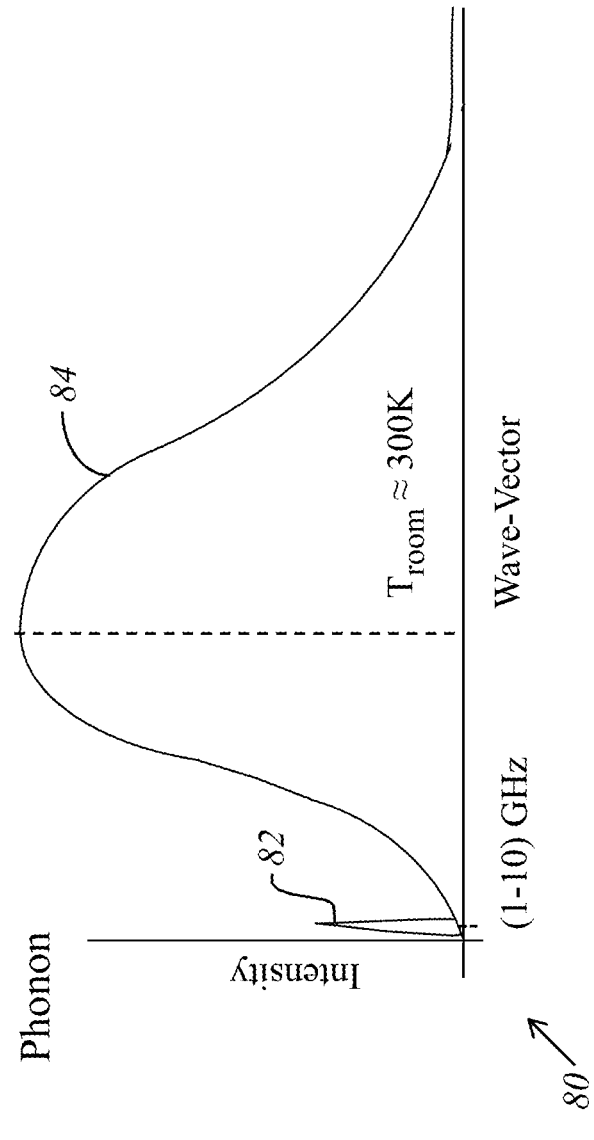
FIG. 4 depicts a peak of non-equilibrium phonons superimposed on Bose-Einstein Spectrum of Equilibrium phonons for the purposes of the present technology.

FIG. 4 depicts a peak 82 of non-equilibrium phonons with frequencies $\omega_k$ in the range of (1-10) 10$^9$ sec$^{-1}$ superimposed on Bose-Einstein Spectrum 84 of Equilibrium phonons.

To conclude, we have shown that generation of high frequency phonons with frequencies f=$\omega/2\pi$ of order of GHz can be achieved in ferromagnetic half-metals, when the conditions for magnon instability are fulfilled.

The main source of phonon damping in half-metals is phonon-electron scattering. From this point of view high $T_c$ ferromagnetic insulators with laser pumping of spin-down electrons would be preferable.

IV. Apparatus for Generating Ultra-High Frequency Sound Waves with Non-Polarized Electrons Injected by Non-Polarized Current Source.

Figure 6:
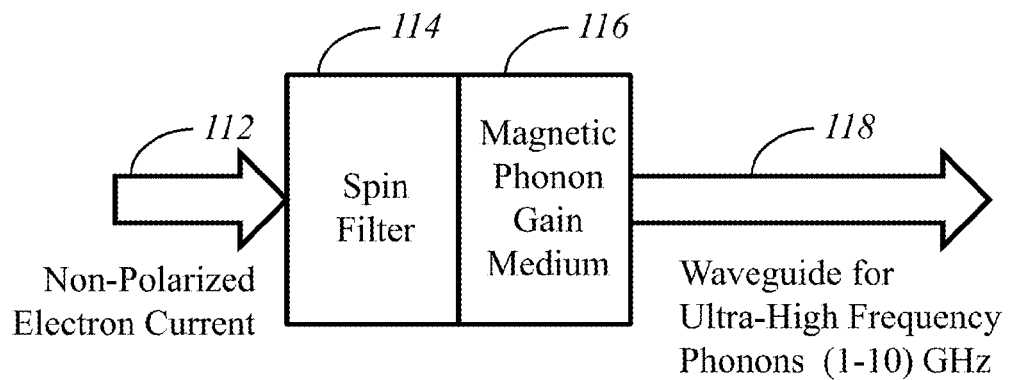
FIG. 6 illustrates an apparatus of the present technology for generation of amplified ultra-high frequency phonons, whereas the non-polarized electrons are injected into the magnetic phonon-gain medium.

FIG. 6 illustrates an apparatus 110 of the present technology for generation of amplified ultra-high frequency phonons comprising a magnetic phonon-gain medium 116.

In an embodiment of the present technology, the magnetic phonon-gain medium 116 is selected from the group consisting of: a ferromagnetic material; a ferromagnetic semiconductor; a ferromagnetic isolator; and a half-metal.

Referring still to FIG. 6, in an embodiment of the present technology, the non-equilibrium electrons having the spin orientation opposite to the direction of magnetization (not shown) of the magnetic phonon-gain medium 116 are injected into the magnetic phonon-gain medium 116 by using the non-polarized electron current source 112 and the spin filter 114.

In an embodiment of the present technology, the spin-filter 114 is configured to spin-filter the applied non-polarized current 112.

More specifically, the spin-filter 114 is in a switch-on position (not shown) for the electrons having the spin orientation opposite to the direction of magnetization of the magnetic phonon-gain medium 116, and in a switch-off position (not shown) for the electrons having the spin orientation along the direction of magnetization of the magnetic phonon-gain medium 116.

In an embodiment of the present technology, the spin-filter 114 is made from a material selected from the group consisting of: a half-metal; a spin-polarized Heusler alloy; $CrO_2$; $Sr_2FeMoO_6$; $Co_2FeAl_{0.5}Si_{0.5}$, and $Fe_3O_4$.

Referring still to FIG. 6, in an embodiment of the present technology, as was explained above, non-equilibrium magnons are generated in the magnetic phonon-gain medium 116 while the non-equilibrium electrons propagate in the magnetic phonon-gain medium 116 and change the spin orientation from the direction opposite to the direction of magnetization (not shown) of the magnetic phonon-gain medium to the direction along to the direction of magnetization of the magnetic phonon-gain medium.

Referring still to FIG. 6, in an embodiment of the present technology, as was explained above, the ultra-high frequency non-equilibrium phonons are generated in the magnetic phonon-gain medium 116 by non-equilibrium magnons having the magnon velocity exceeding the sound velocity in the magnetic phonon-gain medium.

Referring still to FIG. 6, in an embodiment of the present technology, the ultra-high frequency non-equilibrium phonons having frequency f of order of GHz are outputted by using the waveguide 118.

V. Apparatus for Generating Ultra-High Frequency Sound Waves with Polarized Electrons Pumped by Circular Polarized Laser Source.

Figure 7:
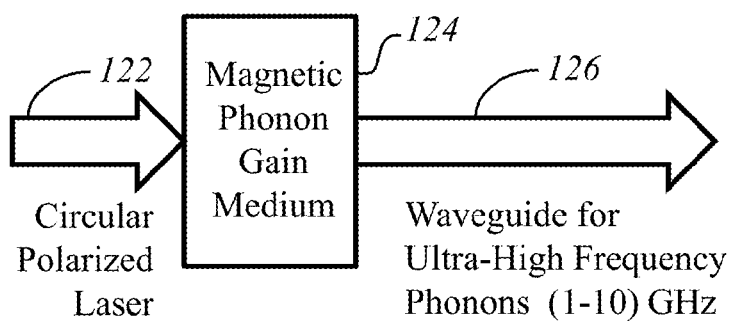
FIG. 7 depicts an apparatus of the present technology for generation of amplified ultra-high frequency phonons, whereas the polarized electrons are pumped into the magnetic phonon-gain medium by using a circular polarized laser.

FIG. 7 depicts the apparatus 120 of the present technology for generation of amplified ultra-high frequency phonons, whereas the polarized electrons are pumped into the magnetic phonon-gain medium 124 by using a circular polarized laser source 122.

Referring still to FIG. 7, in an embodiment of the present technology, as was explained above, non-equilibrium magnons are generated in the magnetic phonon-gain medium 124 while the non-equilibrium electrons propagate in the magnetic phonon-gain medium 124 and change the spin orientation from the direction opposite to the direction of magnetization (not shown) of the magnetic phonon-gain medium to the direction along to the direction of magnetization of the magnetic phonon-gain medium.

Referring still to FIG. 7, in an embodiment of the present technology, as was explained above, the ultra-high frequency non-equilibrium phonons are generated in the magnetic phonon-gain medium 124 by non-equilibrium magnons having the magnon velocity exceeding the sound velocity in the magnetic phonon-gain medium 124.

Referring still to FIG. 7, in an embodiment of the present technology, the ultra-high frequency non-equilibrium phonons having frequency located between (1-10) GHz are outputted by using the waveguide 126.

VI. Apparatus for Generating Ultra-High Frequency Sound Waves with Non-Equilibrium Magnons Injected by Source of Non-Equilibrium Magnons Magnetically Coupled to Magnetic Phonon-Gain Medium.

Figure 8:
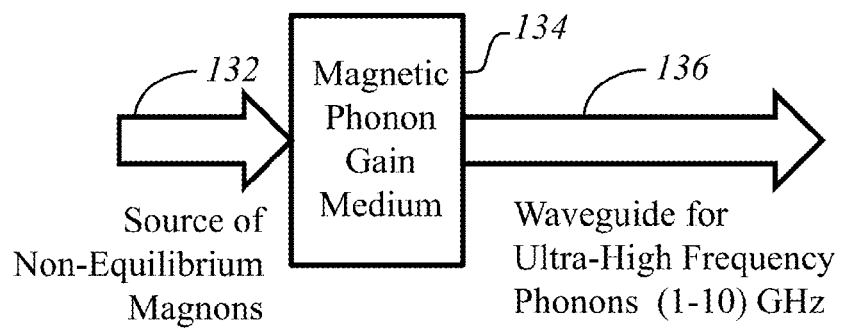
FIG. 8 shows an apparatus of the present technology for generation of amplified ultra-high frequency phonons, whereas the non-equilibrium magnons are injected into the magnetic phonon-gain medium by using a source of non-equilibrium magnons magnetically coupled to the magnetic phonon-gain medium.

FIG. 8 shows the apparatus 130 of the present technology for generation of amplified ultra-high frequency phonons, whereas the non-equilibrium magnons are injected into the magnetic phonon-gain medium 134 by using a source of non-equilibrium magnons 132 magnetically coupled to the magnetic phonon-gain medium 134.

Referring still to FIG. 8, in an embodiment of the present technology, as was explained above, the ultra-high frequency non-equilibrium phonons are generated in the magnetic phonon-gain medium 134 by non-equilibrium magnons having the magnon velocity exceeding the sound velocity in the magnetic phonon-gain medium 134.

Referring still to FIG. 8, in an embodiment of the present technology, the ultra-high frequency non-equilibrium phonons having frequency located in the GHz region are outputted by using the waveguide 136.

VII. Apparatus for Generation of Amplified Ultra-High Frequency Phonons Having K Layers of Magnetic Phonon-Gain Medium.

Figure 9:
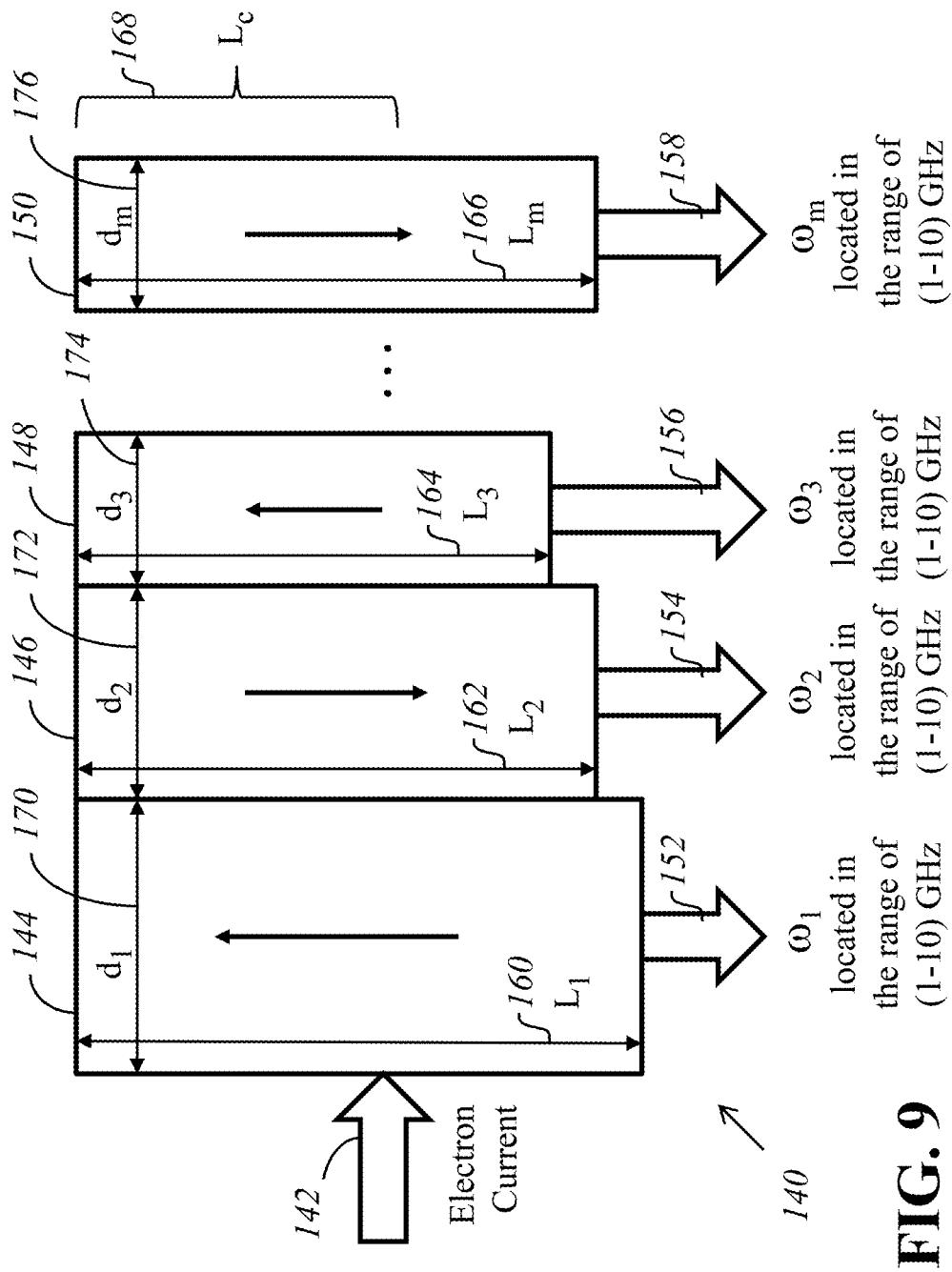
FIG. 9 illustrates an apparatus of the present technology for generation of amplified ultra-high frequency phonons having m layers of magnetic phonon-gain medium, each two neighboring layers having antiparallel magnetization, and having m-output phonon waveguides, each phonon waveguide attached to one layer of magnetic phonon-gain medium in the direction orthogonal to the direction of the electric current.

FIG. 9 illustrates the apparatus 140 of the present technology for generation of amplified ultra-high frequency phonons having m layers of magnetic phonon-gain medium (144, 146, 148, . . . 150), wherein each two neighboring layers include antiparallel magnetization.

Referring still to FIG. 9, in an embodiment of the present technology, more specifically, the apparatus 140 for generating ultra-high frequency sound waves comprises a first magnetic phonon-gain medium layer 144. Non-equilibrium electrons having the spin orientation opposite to the direction of magnetization of the first magnetic phonon-gain medium are injected into the first magnetic phonon-gain medium 144 layer by using the electron current source 142.

As was explained above, non-equilibrium magnons are generated in the first magnetic phonon-gain medium layer 144 while the non-equilibrium electrons propagate in the first magnetic phonon-gain medium layer 144 and change the spin orientation from the direction opposite to the direction of magnetization of the first magnetic phonon-gain medium to the direction along to the direction of magnetization of the first magnetic phonon-gain medium.

As was explained above, the ultra-high frequency non-equilibrium phonons are generated in the first magnetic phonon-gain medium 144 by non-equilibrium magnons having the magnon velocity exceeding the sound velocity in the first magnetic phonon gain medium 144.

Referring still to FIG. 9, in an embodiment of the present technology, more specifically, the apparatus 140 for generating ultra-high frequency sound waves further comprises the second magnetic phonon-gain medium layer 146 coupled to the first magnetic phonon-gain medium layer 144. The second magnetic phonon-gain medium layer includes magnetization directed opposite to the direction of magnetization of the first magnetic phonon gain medium layer 144.

Referring still to FIG. 9, in an embodiment of the present technology, the antiparallel orientation of magnetizations of two neighboring layers can be achieved by using a thin layer of non-magnetic spacer (not shown) of the proper selected width so that the Ruderman-Kittel-Kasuya-Yosida (RKKY) interaction will keep the antiparallel orientation of the two neighboring layers. Indeed, the coupling between thin layers of magnetic materials separated by a non-magnetic spacer material was found to oscillate between ferromagnetic and antiferromagnetic as a function of the distance between the layers.

Referring still to FIG. 9, in an embodiment of the present technology, the electron being a minority electron (that is having spin opposite to the direction of magnetization in the first layer 144) after emitting non-equilibrium magnon becomes a majority electron in the first layer 144, (that is having spin along the direction of magnetization in the first layer 144).

However, a majority electron in the first layer 144 becomes a minority electron in the second layer 146 as its spin is directed opposite to the direction of the magnetization in the second layer 146 and can be re-used again to emit a non-equilibrium magnon in the second layer 146. This process can be repeated as many times as many layers are included in the apparatus 140

Thus, in each layer (144, 146, 148, . . . 150) a non-equilibrium magnon is generated by a non-equilibrium minority electron that propagates through that layer. In each layer a non-equilibrium magnon having velocity exceeding the sound velocity in that layer generates a non-equilibrium phonon having a frequencies located in the GHz region, or in the region between hundreds of MHz to several GHz, depending on the properties of the material.

As shown in FIG. 9, if in each layer the longitudinal dimension is selected exceeding the critical parameter $L_c$ ($L_1$ 160>$L_c$ 168; $L_2$ 162>$L_c$ 168; $L_3$ 164>$L_c$ 168; . . . $L_m$ 166>$L_c$ 168) and the transverse dimension is selected to be less than a critical parameter $L_c$: ($d_1$ 170<$L_c$ 168; $d_2$ 172<$L_c$ 168; $d_3$ 174<$L_c$ 168; . . . $d_m$ 176<$L_c$ 168), each layer can generate in the direction orthogonal to the direction of the electric current high frequency phonons having different frequencies ($\omega_1$ 152; $\omega_2$ 154; $\omega_3$ 156; . . . $\omega_m$ 158); each of these frequencies located in the GHz region, or in the region between hundreds of MHz to several GHz, depending on the properties of the material.

The above discussion has set forth the operation of various exemplary systems and devices, as well as various embodiments pertaining to exemplary methods of operating such systems and devices. In various embodiments, one or more steps of a method of implementation are carried out by a processor under the control of computer-readable and computer-executable instructions. Thus, in some embodiments, these methods are implemented via a computer.

In an embodiment, the computer-readable and computer-executable instructions may reside on computer useable/readable media.

Therefore, one or more operations of various embodiments may be controlled or implemented using computer-executable instructions, such as program modules, being executed by a computer. Generally, program modules include routines, programs, objects, components, data structures, etc., that perform particular tasks or implement particular abstract data types. In addition, the present technology may also be practiced in distributed computing environments where tasks are performed by remote processing devices that are linked through a communications network. In a distributed computing environment, program modules may be located in both local and remote computer-storage media including memory-storage devices. The present technology may also be implemented in real time or in a post-processed or time-shifted implementation where sufficient data is recorded to permit calculation of final results at a later time.

Although specific steps of exemplary methods of implementation are disclosed herein, these steps are examples of steps that may be performed in accordance with various exemplary embodiments. That is, embodiments disclosed herein are well suited to performing various other steps or variations of the steps recited. Moreover, the steps disclosed herein may be performed in an order different than presented, and not all of the steps are necessarily performed in a particular embodiment.

Although various electronic and software based systems are discussed herein, these systems are merely examples of environments that might be utilized, and are not intended to suggest any limitation as to the scope of use or functionality of the present technology. Neither should such systems be interpreted as having any dependency or relation to any one or combination of components or functions illustrated in the disclosed examples.

Although the subject matter has been described in a language specific to structural features and/or methodological acts, the subject matter defined in the appended claims is not necessarily limited to the specific features or acts described above. Rather, the specific features and acts described above are disclosed as exemplary forms of implementing the claims.

What is claimed is:

1. A method of generation of ultra-high frequency sound waves comprising:
   (A) injecting non-equilibrium electrons into a magnetic phonon-gain medium; said injected non-equilibrium electrons having the spin orientation opposite to the direction of magnetization of said magnetic phonon-gain medium;
   (B) generating non-equilibrium magnons in said magnetic phonon-gain medium; wherein said non-equilibrium magnons are generated in said magnetic phonon-gain medium while said non-equilibrium electrons propagate in said magnetic phonon-gain medium and change the spin orientation from the direction opposite to the direction of magnetization of said magnetic phonon-gain medium to the direction along to the direction of magnetization of said magnetic phonon-gain medium; and
   (C) generating ultra-high frequency non-equilibrium phonons in said magnetic phonon-gain medium; wherein said ultra-high frequency non-equilibrium phonons are generated in said magnetic phonon-gain medium by non-equilibrium magnons having the magnon velocity exceeding the sound velocity in said magnetic phonon-gain medium; said non-equilibrium magnons having the magnon velocity exceeding the sound velocity in said magnetic phonon-gain medium being generated by said injected non-equilibrium electrons having spin opposite to the direction of magnetization of said magnetic phonon-gain medium.

2. The method of claim 1, wherein said step (A) further comprises:
   (A1) placing said magnetic phonon-gain medium into a thermostat to maintain temperature of said magnetic phonon-gain medium below a critical temperature.

3. The method of claim 1, wherein said step (A) further comprises:
   (A2) selecting said magnetic phonon-gain medium from the group consisting of:
   a ferromagnetic material; a ferromagnetic semiconductor; a ferromagnetic isolator; and a half-metal.

4. The method of claim 1, wherein said step (A) further comprises:
   (A3) applying an electron current to said magnetic phonon-gain medium; said electron current including electrons having the spin orientation along the direction of magnetization of said magnetic phonon-gain medium; said current also including electrons having the spin orientation opposite to the direction of magnetization of said magnetic phonon-gain medium; wherein only electrons having the spin orientation opposite to the direction of magnetization of said magnetic phonon-gain medium participate in the generation of non-equilibrium magnons in said magnetic phonon-gain medium.

5. The method of claim 1, wherein said step (A) further comprises:
   (A4) injecting non-equilibrium electrons into said magnetic phonon-gain medium by using a source of spin-oriented current; wherein said source of spin-oriented current injects non-equilibrium electrons having the spin orientation opposite to the direction of magnetization of said magnetic phonon-gain medium.

6. The method of claim 5, wherein said step (A4) further comprises:
   (A4, 1) injecting non-equilibrium electrons into said magnetic phonon-gain medium by attaching a spin-filter coupled between said magnetic phonon-gain medium and a source of applied electron current; wherein said spin-filter is configured to spin-filter the applied electron current; and wherein said spin-filter is in a switch-on position for the electrons having the spin orientation opposite to the direction of magnetization of said magnetic phonon-gain medium; and wherein said spin-filter is in a switch-off position for the electrons having the spin orientation along the direction of magnetization of said magnetic phonon-gain medium.

7. The method of claim 6, wherein said step (A4, 1) further comprises:
   (A4, 1, 1) selecting said spin filter from the group consisting of:
   a half-metal; a spin-polarized Heusler alloy; $CrO_2$; $Sr_2FeMoO_6$; $Co_2FeAl_{0.5}Si_{0.5}$, and $Fe_3O_4$.

8. The method of claim 1, wherein said step (A) further comprises:
   (A5) pumping electrons into said magnetic phonon-gain medium; said electrons having the spin orientation along the direction of magnetization of said magnetic phonon-gain medium and also having the spin orientation opposite to the direction of magnetization of said magnetic phonon-gain medium; wherein only electrons having the spin orientation opposite to the direction of magnetization of said magnetic phonon-gain medium participate in the generation of non-equilibrium magnons in said magnetic phonon-gain medium.

9. The method of claim 1, wherein said step (A) further comprises:
   (A6) pumping into said magnetic phonon-gain medium polarized non-equilibrium electrons having the spin orientation opposite to the direction of magnetization of said magnetic phonon-gain medium by using a circularly polarized laser source.

10. The method of claim 1, wherein said step (B) further comprises:
    (B1) increasing the number of said non-equilibrium magnons by increasing the number of said non-equilibrium electrons in said magnetic phonon-gain medium; said non-equilibrium electrons having the spin orientation opposite to the direction of magnetization of said magnetic phonon-gain medium.

11. The method of claim 1, wherein said step (C) further comprises:
    (C1) achieving the threshold level of non-equilibrium phonons instability in said magnetic phonon-gain medium by reaching the threshold number of said nonequilibrium magnons; wherein the rate of non-equilibrium phonons generation exceeds the rate of non-equilibrium phonons relaxation in said magnetic phonon-gain medium; wherein an amplified stream of ultra-high frequency sound is generated.

12. The method of claim 11, wherein said step (C1) further comprises:
(C1, 1) generating said amplified stream of ultra-high frequency sound having a frequency located in the range between 1 GHz and 10 GHz.

13. The method of claim 11, wherein said step (C1) further comprises:
(C1, 2) changing the frequency of said generated amplified stream of ultra-high frequency sound by changing the geometrical dimensions of said magnetic phonon-gain medium.

14. The method of claim 1 further comprising:
(D) outputting said generated amplified stream of ultra-high frequency sound into an external ultra-high frequency sound wave-guide attached to a surface area of said magnetic phonon-gain medium.

15. A method of generation of ultra-high frequency sound waves comprising:
(A) injecting non-equilibrium magnons into a magnetic phonon-gain medium by using a source of non-equilibrium magnons magnetically coupled to said magnetic phonon-gain medium;
and
(B) generating ultra-high frequency non-equilibrium phonons in said magnetic phonon-gain medium; wherein said ultra-high frequency non-equilibrium phonons are generated in said magnetic phonon-gain medium by injected non-equilibrium magnons having the magnon velocity exceeding the sound velocity in said magnetic phonon-gain medium.

16. The method of claim 15, wherein said step (A) further comprises:
(A1) selecting said magnetic phonon-gain medium from the group consisting of:
a ferromagnetic material; a ferromagnetic semiconductor; a ferromagnetic isolator; and a half-metal.

17. The method of claim 15, wherein said step (B) further comprises:
(B1) achieving the threshold level of non-equilibrium phonons instability in said magnetic phonon-gain medium when the rate of non-equilibrium phonons generation exceeds the rate of non-equilibrium phonons relaxation in said magnetic phonon-gain medium; wherein an amplified stream of ultra-high frequency sound is generated.

18. The method of claim 17, wherein said step (B1) further comprises:
(B1, 1) generating said amplified stream of ultra-high frequency sound having a frequency located in the range between 1 GHz and 10 GHz.

19. The method of claim 17, wherein said step (B1) further comprises:
(B1, 2) changing the frequency of said generated amplified stream of ultra-high frequency sound by changing the geometrical dimensions of said magnetic phonon-gain medium.

20. The method of claim 15 further comprising:
(C) outputting said generated amplified stream of ultra-high frequency sound into an external ultra-high frequency sound wave-guide attached to a surface area of said magnetic phonon-gain medium.

21. An apparatus for generating ultra-high frequency sound waves comprising:
(A) a magnetic phonon-gain medium; wherein non-equilibrium electrons having the spin orientation opposite to the direction of magnetization of said magnetic phonon-gain medium are injected into said magnetic phonon-gain medium; wherein non-equilibrium magnons are generated in said magnetic phonon-gain medium while said non-equilibrium electrons propagate in said magnetic phonon-gain medium and change the spin orientation from the direction opposite to the direction of magnetization of said magnetic phonon-gain medium to the direction along to the direction of magnetization of said magnetic phonon-gain medium; wherein said ultra-high frequency non-equilibrium phonons are generated in said magnetic phonon-gain medium by non-equilibrium magnons having the magnon velocity exceeding the sound velocity in said magnetic phonon-gain medium; said non-equilibrium magnons having the magnon velocity exceeding the sound velocity in said magnetic phonon-gain medium being generated by said injected non-equilibrium electrons having spin opposite to the direction of magnetization of said magnetic phonon-gain medium;
and
(B) means for outputting said ultra-high frequency non-equilibrium phonons generated in said magnetic phonon-gain medium by non-equilibrium magnons having the magnon velocity exceeding the sound velocity in said magnetic phonon-gain medium.

22. The apparatus of claim 21 further comprising:
(C) a thermostat; said magnetic phonon-gain medium placed into said thermostat; said thermostat configured to maintain temperature of said magnetic phonon-gain medium below a critical temperature.

23. The apparatus of claim 21 further comprising:
(D) a source of current configured to inject into said magnetic phonon-gain medium electrons having the spin orientation along the direction of magnetization of said magnetic phonon-gain medium; and configured to inject into said magnetic phonon-gain medium electrons having the spin orientation opposite to the direction of magnetization of said magnetic phonon-gain medium; wherein only electrons having the spin orientation opposite to the direction of magnetization of said magnetic phonon-gain medium participate in the generation of non-equilibrium magnons in said magnetic phonon-gain medium.

24. The apparatus of claim 21 further comprising:
(E) a source of spin-oriented current configured to inject into said magnetic phonon-gain medium non-equilibrium electrons having the spin orientation opposite to the direction of magnetization of said magnetic phonon-gain medium.

25. The apparatus of claim 21 further comprising:
(F) a spin-filter coupled between said magnetic phonon-gain medium and a source of applied electron current; wherein said spin-filter is configured to spin-filter the applied electron current; and wherein said spin-filter is in a switch-on position for the electrons having the spin orientation opposite to the direction of magnetization of said magnetic phonon-gain medium; and wherein said spin-filter is in a switch-off position for the electrons having the spin orientation along the direction of magnetization of said magnetic phonon-gain medium.

26. The apparatus of claim 25, wherein said spin filter is selected from the group consisting of:
a half-metal; a spin-polarized Heusler alloy; $CrO_2$; $Sr_2FeMoO_6$; $Co_2FeAl_{0.5}Si_{0.5}$, and $Fe_3O_4$.

27. The apparatus of claim 21 further comprising:
(G) a pumping source configured to pump electrons having the spin orientation along the direction of magnetization of said magnetic phonon-gain medium; and configured to pump electrons having the spin orientation opposite to the direction of magnetization of said magnetic phonon-gain medium; wherein only electrons having the spin orientation opposite to the direction of magnetization of said magnetic phonon-gain medium participate in the generation of non-equilibrium magnons in said magnetic phonon-gain medium.

28. The apparatus of claim 21 further comprising:
(I) a circularly polarized laser source configured to pump into said spintronic material polarized non-equilibrium electrons having the spin orientation opposite to the direction of magnetization of said magnetic phonon-gain medium.

29. The apparatus of claim 21, wherein said means (B) further comprises:
(B1) an external ultra-high frequency sound wave-guide attached to a surface area of said magnetic phonon-gain medium; wherein said external ultra-high frequency sound wave-guide is configured to output an amplified stream of ultra-high frequency sound; said amplified stream of ultra-high frequency sound having a frequency located in the range between 1 GHz and 10 GHz.

30. An apparatus for generating ultra-high frequency sound waves comprising:
(A) a magnetic phonon-gain medium;
(B) a source of non-equilibrium magnons magnetically coupled to said magnetic phonon-gain medium; wherein non-equilibrium magnons having the magnon velocity exceeding the sound velocity are injected into said magnetic phonon-gain medium; and wherein ultra-high frequency non-equilibrium phonons are generated in said magnetic phonon-gain medium by said injected non-equilibrium magnons having the magnon velocity exceeding the sound velocity in said magnetic phonon-gain medium;
and
(C) means for outputting said ultra-high frequency non-equilibrium phonons generated in said magnetic phonon-gain medium by non-equilibrium magnons having the magnon velocity exceeding the sound velocity in said magnetic phonon-gain medium.

31. The apparatus of claim 30 further comprising:
(D) a thermostat; said magnetic phonon-gain medium placed into said thermostat; said thermostat configured to maintain temperature of said magnetic phonon-gain medium below a critical temperature.

32. The apparatus of claim 30, wherein said means (C) further comprises:
(C1) an external ultra-high frequency sound wave-guide attached to a surface area of said magnetic phonon-gain medium; wherein said external ultra-high frequency sound wave-guide is configured to output an amplified stream of ultra-high frequency sound; said amplified stream of ultra-high frequency sound having a frequency located in the range between 1 GHz and 10 GHz.

33. An apparatus for generating ultra-high frequency sound waves comprising:
(A) a first magnetic phonon-gain medium; wherein non-equilibrium electrons having the spin orientation opposite to the direction of magnetization of said first magnetic phonon-gain medium are injected into said first magnetic phonon-gain medium; wherein non-equilibrium magnons are generated in said first magnetic phonon-gain medium while said non-equilibrium electrons propagate in said first magnetic phonon-gain medium and change the spin orientation from the direction opposite to the direction of magnetization of said first magnetic phonon-gain medium to the direction along to the direction of magnetization of said first magnetic phonon-gain medium; wherein said ultra-high frequency non-equilibrium phonons are generated in said first magnetic phonon-gain medium by non-equilibrium magnons having the magnon velocity exceeding the sound velocity in said first magnetic phonon gain medium; said non-equilibrium magnons having the magnon velocity exceeding the sound velocity in said first magnetic phonon-gain medium being generated by said injected non-equilibrium electrons having spin opposite to the direction of magnetization of said first magnetic phonon-gain medium;

(B) a second magnetic phonon-gain medium coupled to said first magnetic phonon-gain medium; said second magnetic phonon-gain medium having magnetization directed opposite to the direction of magnetization of said first magnetic phonon gain medium;
wherein said non-equilibrium electrons after generating non-equilibrium magnons in said first spintronic magnetic changing their spin orientation; and wherein said non-equilibrium electrons entering said second spintronic magnetic with the spin orientation opposite to the direction of magnetization of said second magnetic phonon-gain medium;
wherein non-equilibrium magnons are generated in said second magnetic phonon-gain medium while said non-equilibrium electrons propagate in said second magnetic phonon-gain medium and change the spin orientation from the direction opposite to the direction of magnetization of said second magnetic phonon-gain medium to the direction along to the direction of magnetization of said second magnetic phonon-gain medium; wherein said ultra-high frequency non-equilibrium phonons are generated in said second magnetic phonon-gain medium by non-equilibrium magnons having the magnon velocity exceeding the sound velocity in said second magnetic phonon gain medium; said non-equilibrium magnons having the magnon velocity exceeding the sound velocity in said second magnetic phonon-gain medium being generated by said injected non-equilibrium electrons having spin opposite to the direction of magnetization of said second magnetic phonon-gain medium;
and
(C) an m-magnetic phonon-gain medium coupled to a (m−1)-magnetic phonon-gain medium; said m-magnetic phonon-gain medium having magnetization directed opposite to the direction of magnetization of said (m−1)-magnetic phonon gain medium; m being an integer;
wherein said non-equilibrium electrons after generating non-equilibrium magnons in said (m−1)-spintronic magnetic changing their spin orientation; and wherein said non-equilibrium electrons entering said m-spintronic magnetic with the spin orientation opposite to the direction of magnetization of said m-magnetic phonon-gain medium;
wherein non-equilibrium magnons are generated in said m-magnetic phonon-gain medium while said non-equilibrium electrons propagate in said m-magnetic phonon-gain medium and change the spin orientation from the direction opposite to the direction of magnetization of said m-magnetic phonon-gain medium to the direction along to the direction of magnetization of said m-magnetic phonon-gain medium; wherein said ultra-high frequency non-equilibrium phonons are generated in said m-magnetic phonon-gain medium by non-equilibrium magnons having the magnon velocity exceeding the sound velocity in said m-magnetic material; said non-equilibrium magnons having the magnon velocity exceeding the sound velocity in said m-magnetic phonon-gain medium being generated by said injected non-equilibrium electrons having spin opposite to the direction of magnetization of said m-magnetic phonon-gain medium.

34. The apparatus of claim 33, wherein the transverse direction is aligned with the direction of the injected electric current; wherein said first magnetic phonon-gain medium further comprises a strip of material having a first transverse dimension being less than a critical parameter $L_c$ and having a first longitudinal dimension exceeding said critical parameter $L_c$; further comprising:
 a first external ultra-high frequency sound wave-guide attached to a surface area of said first magnetic phonon-gain medium in the longitudinal direction; wherein said first external ultra-high frequency sound wave-guide is configured to output a first amplified stream of ultra-high frequency sound; said first amplified stream of ultra-high frequency sound having a first frequency located in the range between 1 GHz and 10 GHz.

35. The apparatus of claim 33, wherein the transverse direction is aligned with the direction of the injected electric current; wherein said second magnetic phonon-gain medium further comprises a strip of material having a second transverse dimension being less than a critical parameter $L_c$ and having a second longitudinal dimension exceeding said critical parameter $L_c$; further comprising:
 a second external ultra-high frequency sound wave-guide attached to a surface area of said first magnetic phonon-gain medium in the longitudinal direction; wherein said second external ultra-high frequency sound wave-guide is configured to output a second amplified stream of ultra-high frequency sound; said second amplified stream of ultra-high frequency sound having a second frequency located in the range between 1 GHz and 10 GHz.

36. The apparatus of claim 33, wherein the transverse direction is aligned with the direction of the injected electric current; wherein said m-magnetic phonon-gain medium further comprises a strip of material having an m-transverse dimension less than a critical parameter $L_c$ and having an m-longitudinal dimension exceeding said critical parameter $L_c$; further comprising:
 an m-external ultra-high frequency sound wave-guide attached to a surface area of said m-magnetic phonon-gain medium in the longitudinal direction; wherein said m-external ultra-high frequency sound wave-guide is configured to output a m-amplified stream of ultra-high frequency sound; said m-amplified stream of ultra-high frequency sound having a m-frequency located in the range between 1 GHz and 10 GHz.

* * * * *